(12) United States Patent
Lawrence et al.

(10) Patent No.: US 8,395,378 B2
(45) Date of Patent: Mar. 12, 2013

(54) NONDESTRUCTIVE ROBOTIC INSPECTION METHOD AND SYSTEM THEREFOR

(75) Inventors: Wayne Lee Lawrence, Sardinia, OH (US); Michael Dziech, Cincinnati, OH (US); Joseph A. Traxler, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 357 days.

(21) Appl. No.: 12/769,742

(22) Filed: Apr. 29, 2010

(65) Prior Publication Data

US 2011/0267047 A1 Nov. 3, 2011

(51) Int. Cl.
*G01N 27/82* (2006.01)
(52) U.S. Cl. .................. 324/238; 324/239; 324/240
(58) Field of Classification Search .................. 324/238, 324/239, 240, 262
See application file for complete search history.

(56) References Cited

U.S. PATENT DOCUMENTS

| | | | | |
|---|---|---|---|---|
| 5,465,045 A * | 11/1995 | DeRock | ........... | 324/220 |
| 5,834,937 A * | 11/1998 | Burris | ........... | 324/219 |
| 6,288,537 B1* | 9/2001 | Viertl et al. | ........... | 324/230 |
| 6,895,066 B1* | 5/2005 | Busch et al. | ........... | 376/258 |
| 7,068,029 B2* | 6/2006 | Hatcher et al. | ........... | 324/239 |
| 7,190,162 B2* | 3/2007 | Tenley et al. | ........... | 324/238 |
| 7,657,389 B2* | 2/2010 | Suh et al. | ........... | 702/104 |
| 7,659,715 B2* | 2/2010 | Briffa et al. | ........... | 324/240 |
| 2004/0051525 A1 | 3/2004 | Hatcher et al. | | |
| 2004/0056656 A1 | 3/2004 | McKnight et al. | | |
| 2005/0200355 A1 | 9/2005 | Hatcher et al. | | |
| 2006/0017434 A1 | 1/2006 | Tenley et al. | | |
| 2006/0229833 A1 | 10/2006 | Pisupati et al. | | |
| 2006/0280604 A1 | 12/2006 | Roney et al. | | |
| 2007/0096728 A1 | 5/2007 | Mader Viertl | | |
| 2007/0244659 A1 | 10/2007 | Suh et al. | | |
| 2007/0272042 A1 | 11/2007 | Goldfine et al. | | |
| 2009/0115410 A1 | 5/2009 | McKnight et al. | | |

FOREIGN PATENT DOCUMENTS

EP 1990637 A2 * 11/2008

* cited by examiner

*Primary Examiner* — Patrick Assouad
*Assistant Examiner* — Christopher McAndrew
(74) *Attorney, Agent, or Firm* — General Electric Company; Sushupta T. Sudarshan; David J. Clement

(57) ABSTRACT

A method and system for inspecting components, such as a rotating component of a turbomachines having one or more slots along a perimeter thereof. The method entails mounting to a robotic apparatus a probe assembly that includes a holder assembly to which a probe tip is mounted, an eddy current coil within the probe tip and adjacent a first face thereof, a touch probe contact located at a second face of the probe tip, an element for enabling relative movement between the probe tip and holder assembly, and an element for biasing the probe tip relative to the holder assembly in a direction parallel to the movement. The probe tip is then placed in a slot and caused to travel along the surface of the slot to electromagnetically inspect the slot for cracks in its surface while the first face of the probe tip is maintained in contact with a slot surface.

18 Claims, 3 Drawing Sheets

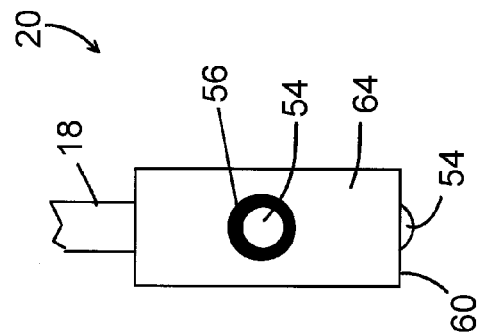
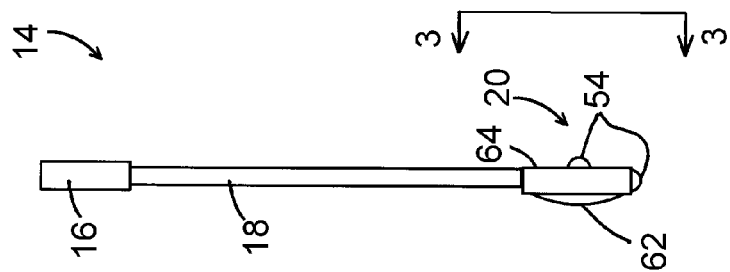
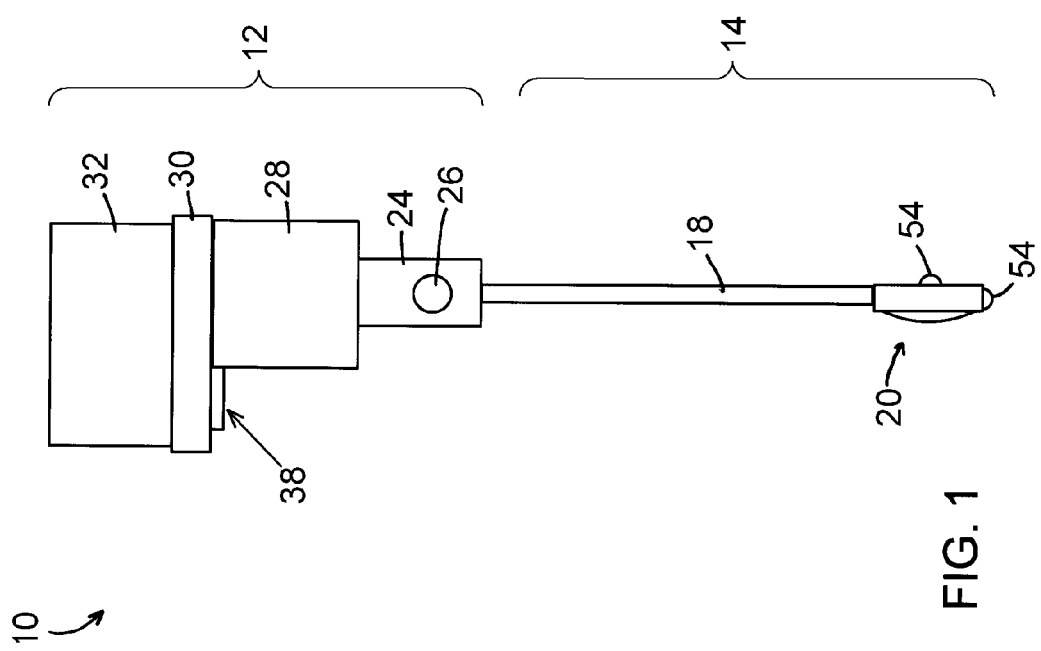

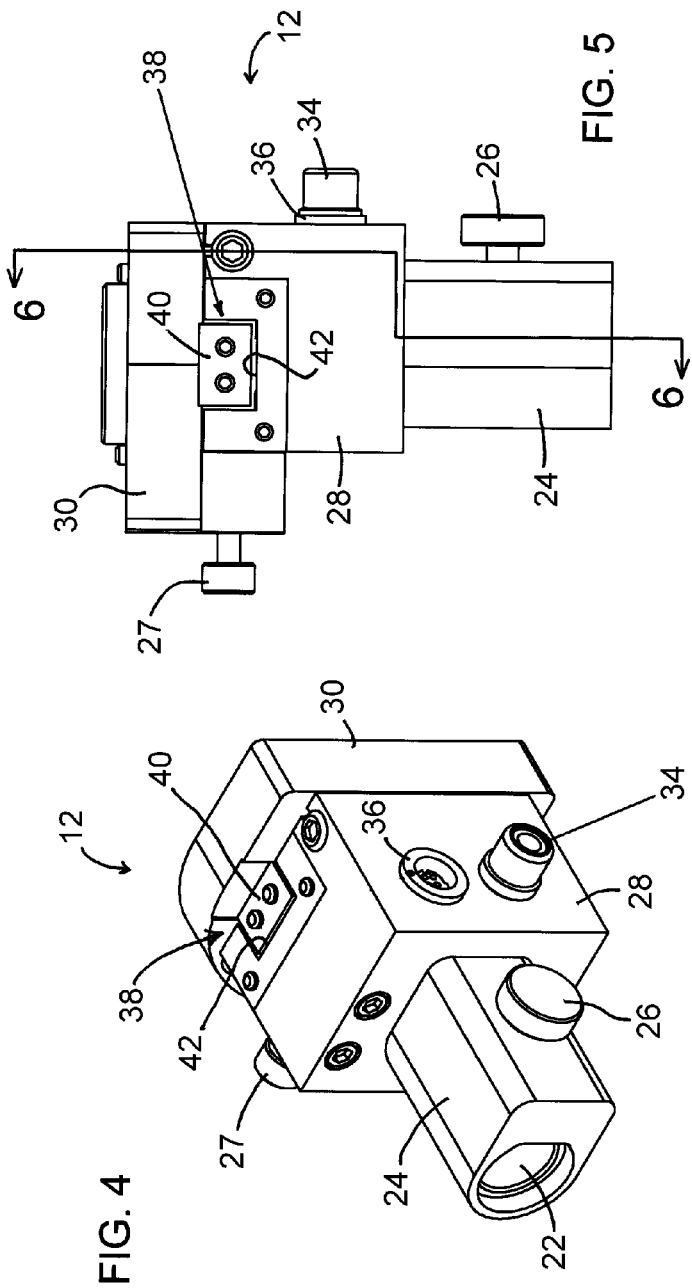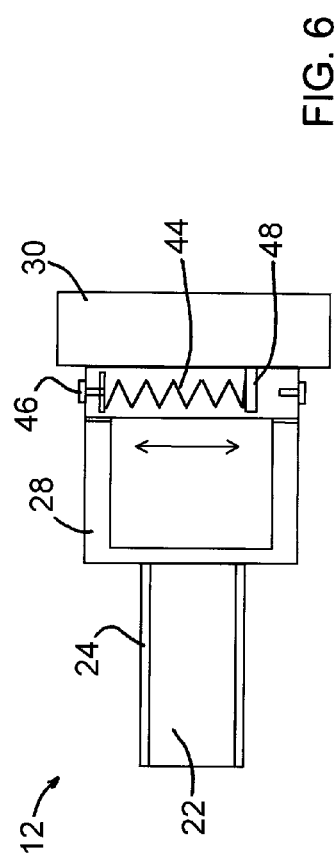

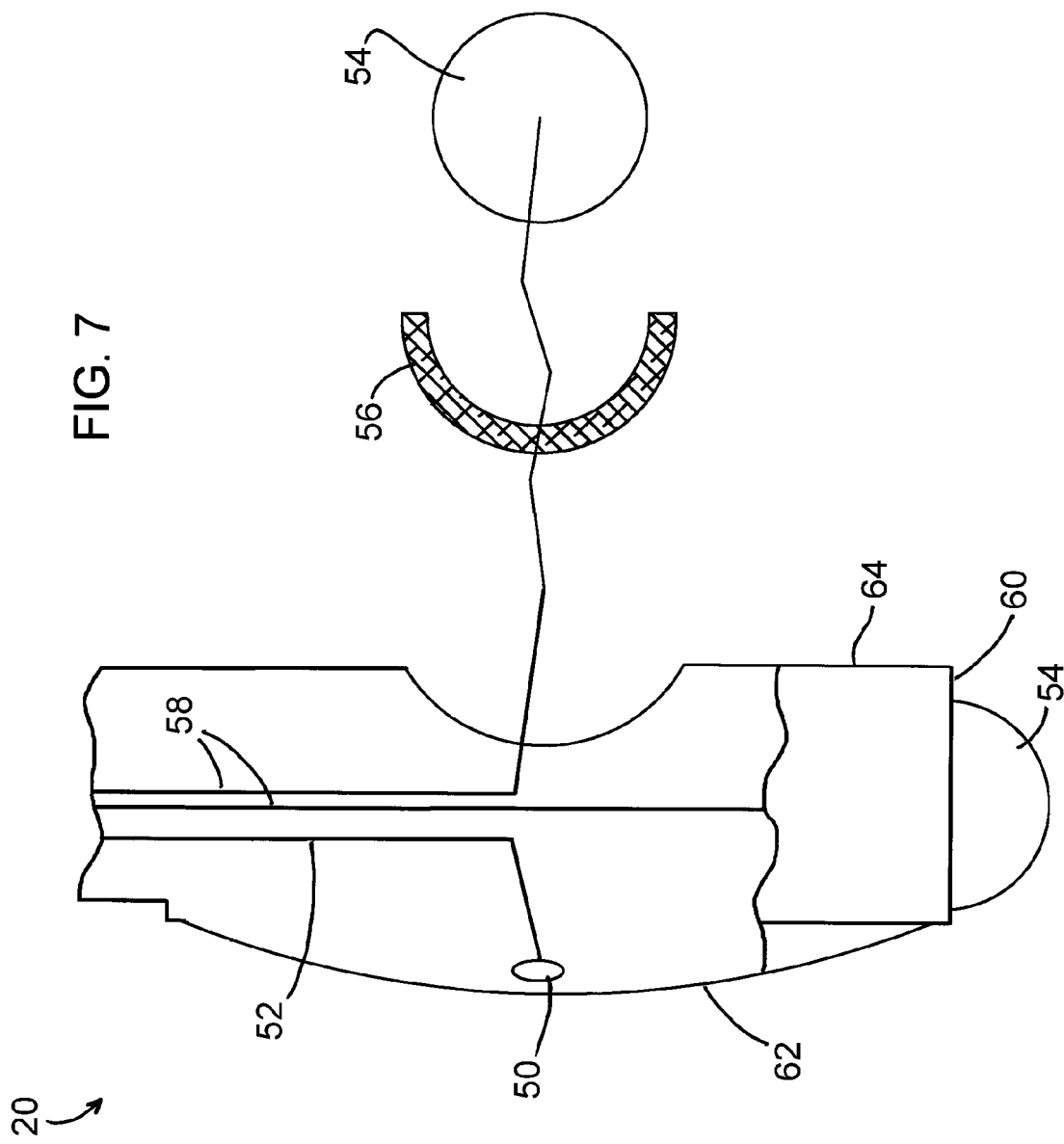

NONDESTRUCTIVE ROBOTIC INSPECTION METHOD AND SYSTEM THEREFOR

BACKGROUND OF THE INVENTION

The present invention generally relates to nondestructive inspection methods and systems. More particularly, this invention relates to a method and system that enables automated scanning with an eddy current probe, such as for the purpose of inspecting rotating components of turbomachines.

Various nondestructive examination (NDE) techniques have been used to perform nondestructive testing on articles. An example is eddy current probe inspection of turbine components, as disclosed in commonly-assigned U.S. Pat. Nos. 4,706,020, 6,426,622, 6,545,467 and 6,952,094, whose disclosures pertaining to the construction, operation, and use of eddy current probes are incorporated herein by reference. Components of particular interest include rotating components of gas turbines, such as the high pressure turbine (HPT) disks of gas turbine engines. In the hostile operating environment of a gas turbine engine, the structural integrity of a turbine disk within its turbine section is of great importance in view of the high mechanical stresses that the disk must be able to continuously withstand at high temperatures and rotational speeds. The blades of a turbine disk are secured in slots, typically in the form of what are known as dovetail slots, which tend to eventually form cracks over time and must therefore be monitored when opportunities arise. The ability to detect cracks with lengths of as little as 60 mils (about 1.5 mm) and even less is desirable in order to provide sufficiently early detection to avoid catastrophic failure of a turbine disk.

Since turbine disks are inspected on a regular schedule, inspection techniques that minimize downtime are preferred to reduce operating costs. Common methods of inspecting turbine disks involve handheld or semi-automated systems, which typically have inherent problems, shortcomings or disadvantages. Handheld inspection methods are prone to user-related issues that can affect the quality of the signal. As an example, an eddy current probe may tilt relative to the surface being scanned when the probe is scanned to an edge or corner of a slot, resulting in erroneous readings. Though semi-automated inspection equipment are generally capable of overcoming user-related issues of handheld methods, existing equipment are often expensive and slow due to the custom tooling needed for each part to be inspected. As such, a fully-automated method and system would be preferred in order to reduce downtime and improve the reliability of the turbine disk inspections.

BRIEF DESCRIPTION OF THE INVENTION

The present invention provides a method and system for inspecting components, such as a rotating component of a turbomachines having one or more slots along a perimeter thereof. The method and system make use of an eddy current probe that is sized and configured to be placed in the slot and electromagnetically inspect the slot for cracks in surfaces thereof as the probe travels through the slot.

According to a first aspect of the invention, the inspection method generally entails mounting to a robotic apparatus a probe assembly that includes a holder assembly to which a probe tip is mounted, an eddy current coil within the probe tip and adjacent a first face thereof, a touch probe contact located at a second face of the probe tip, means for enabling relative movement between the probe tip and the holder assembly, and means for biasing the probe tip relative to the holder assembly in a direction parallel to the movement enabled by the enabling means. The eddy current probe tip of the probe assembly is then placed in the slot, and the first face of the probe tip is caused to contact and travel along the surface of the slot and the eddy current coil is caused to electromagnetically inspect the slot for cracks in the surface thereof. The biasing means and the enabling means maintain the first face of the probe tip in contact with the surface of the slot as the probe tip travels through the slot.

According to a second aspect of the invention, the inspection system generally includes a probe assembly configured for mounting to a robotic apparatus. The probe assembly comprises a holder assembly to which a probe tip is mounted, an eddy current coil within the probe tip and adjacent a first face thereof, a touch probe contact located at a second face of the probe tip, means for enabling relative movement between the probe tip and the holder assembly, and means for biasing the probe tip relative to the holder assembly in a direction parallel to the movement enabled by the enabling means. The biasing means and the enabling means are adapted to maintain the first face of the probe tip in contact with a surface of the slot as the probe tip travels through the slot.

A technical effect of this invention is that slots in a turbomachine rotating component, such as a turbine disk, can be quickly electromagnetically scanned for cracks without user issues and without the need for custom tooling for each part to be inspected.

Other aspects and advantages of this invention will be better appreciated from the following detailed description.

BRIEF DESCRIPTION OF THE DRAWINGS

FIG. 1 is a side view of a probe assembly including a probe holder assembly and eddy current probe unit in accordance with a preferred embodiment of the invention.

FIG. 2 is an isolated side view of the eddy current probe unit of FIG. 1.

FIG. 3 is a side view of a probe tip of the probe unit of FIG. 2.

FIGS. 4 and 5 are isolated perspective and side views of the probe holder assembly of FIG. 1.

FIG. 6 is a cross-sectional view of the probe holder assembly along section line 6-6 of FIG. 5.

FIG. 7 is an exploded view of the probe tip of FIGS. 1 through 3.

DETAILED DESCRIPTION OF THE INVENTION

FIG. 1 depicts an eddy current probe assembly 10 configured for performing a nondestructive examination (NDE) of a turbomachine rotating component, such as a turbine disk (not shown), in accordance with a preferred embodiment of this invention. The particular embodiment of the invention shown in FIG. 1 and described below is adapted to enable automated inspection of dovetail slots (not shown) in the perimeter of a turbomachine rotating component, which may be parallel or offset by some acute angle to the rotational axis of the component. While the probe assembly 10 will be described in reference to the inspection of dovetail slots in turbine disks, the invention is not limited to this application, but can be used to inspect various other types of hardware.

The probe assembly 10 is represented in FIG. 1 as comprising a probe holder assembly 12 to which is mounted a probe unit 14. One end of the probe unit 14 is configured as a connector 16 (FIG. 2), which is received within a bore 22 (FIGS. 4 and 6) in a probe holder end 24 of the holder assembly 12 and removably secured within the bore 22 by a thumb screw 26. The connector 16 is mounted to one end of a stem 18 of the probe unit 14, and an eddy current probe tip 20 is mounted on the opposite end of the stem 18. The holder assembly 12 further comprises a housing 28 to which the holder end 24 is mounted, and a base 30 to which the housing 28 is mounted. A robotic tooling portion 32 is shown in FIG. 1 as attached to the base 30, by which the probe holder assembly 12 as well as the entire probe assembly 10 is able to be connected to a robotic controller (not shown). The robotic controller can be part of a robotic apparatus of any suitable type known in the art, and therefore will not be described in any detail here. The probe holder assembly 12 is further equipped with connectors 34 and 36, designated herein as a touch contact connector 34 and an eddy current connector 36. The connectors 34 and 36 enable, respectively, a robotic control software system (not shown) and an eddy current analysis software system (not shown) to be connected through the holder assembly 12 to the probe tip 20. Various materials can be used to fabricate the holder end 24, housing 28 and base of the holder assembly 12 and the connector 16, stem 18 and probe tip 20 of the probe unit 14. Preferred materials are electrically conductive, a nonlimiting example being aluminum alloys.

As represented in FIG. 7, the probe tip 20 comprises at least one eddy current coil 50 located adjacent and oriented normal to a first longitudinal face 62 of the probe tip 20. The coil(s) 50 can be of any type suitable for use in eddy current scanning, such as a ferrite-shielded probe coil available from Uniwest. Furthermore, the eddy current sensing technique used may be an absolute or differential sensing technique. Electrical connection to the test coil 50 is made through a cable 52 that is routed through the probe stem 18 and connector 16 to the probe holder housing 28 and eddy current connector 36.

As depicted in FIGS. 3 and 7, the probe tip 20 further comprises a pair of touch probe contacts 54 located on two of its adjoining faces, one of which is a distal or end face 60 of the tip 20 while the other is a second longitudinal face 64 of the tip 20 opposite the first face 62 at which the one or more eddy current coils 50 are located. As shown in FIG. 7, each contact 54 can be configured as a spherical ball that is held in a cup 56. According to a preferred aspect of the invention, the cups 56 are formed of an electrical insulation material to electrically insulate their contacts 54 from the remainder of the probe tip 20. The contacts 54 are formed of an electrically conductive and wear-resistant material, such as stainless steel, which is connected to electrical ground by cables 58 routed through the probe stem 18 and connector 16 to the probe holder housing 28 and contact connector 34. Through these connections, the robotic control software system can be employed to analyze data received from the contacts 54 regarding the contact between the contacts 54 and surfaces of a dovetail slot being inspected with the probe assembly 10. The insulating cups 56 insulate the contacts 54 from the remainder of the probe tip 20 because the probe tip 20 is connected to ground through its connection to the probe stem 18, probe connector 16, and probe holder assembly 12 to the robotic controller, and the input on the robotic controller is active low (searching for a ground). In this manner, contact between the one of the contacts 54 and the surface of a slot being inspected results in electrical grounding and uploading the position of the probe tip 20 to the robotic controller for enabling the robotic apparatus to make continuous adjustments of the position of the probe tip 20 within the slot. Use of the contacts 54 is generally in the same manner as used for touch probe contacts of the prior art that are adapted to contact a part being inspected and provide feedback as to the position of a probe and enable adjustments to be made to the probe orientation and inspection process as necessary. However, the present invention integrates at least one touch probe contact 54 into the eddy current probe tip 20 itself, which allows the touch probe function to be performed without changing the type of probe and allows adjustments to be made much faster and on the fly. In the preferred embodiment shown, the presence of two (or more) contacts 54 is advantageous if there is limited access to an areas to be inspected, in that a single contact might not be properly located to enable reach or contact with a surface of the part being inspected. Furthermore, the presence of two (or more) contacts reduces the amount of movement required by the probe tip 20 to find locations to be inspected.

During inspection, the first face 62 of the probe tip 20 is maintained in contact with a surface of a dovetail slot. The first face 62 is represented as having a convex shape to better conform to the shape of a dovetail slot surface, though such a shape is not absolutely required. The eddy current coil 50 is oriented normal to the first face 62, and therefore will be substantially normal to a slot surface being inspected to maximize the electrical output signal of the eddy current probe tip 20. To facilitate the use of the probe assembly 10 in a fully automated inspection process, the probe holder assembly 12 is depicted in FIGS. 1, 4 and 5 as comprising a slide assembly 38 that includes a slide 40 attached to the probe base 30 and received in a slot 42 in the probe housing 28. The function of the slide assembly 38 is to enable the first face 62 of the probe tip 20 to be maintained in contact with the slot surface while avoiding tilting of the probe tip 20 relative to the slot. While the slide assembly 38 is shown as a preferred embodiment, it should be evident that various other means could be used to enable relative movement between the probe unit 14 and the holder assembly 12.

Compensation of the position of the probe tip 20 between the position of the robotic controller and the slot surface is achieved by biasing the probe housing 28 relative to the base 30 with a spring 44 or any other suitable type of biasing device. The spring 44 abuts an adjustment screw 46 threaded into the housing 28 and a pin 48 secured to the base 30, urging the housing 28 (and therefore also the probe unit 14 attached thereto) relative to the base 30 in a direction parallel to the slide 40. In the embodiment shown in the figures, the eddy current coil 50 is located adjacent the first longitudinal face 62 of the probe tip 20 and therefore is preferably maintained in contact with the slot surface as a result of the slide assembly 38 biasing the probe tip 20 in a direction normal to the longitudinal face 62. An advantage of the biased slide assembly 38 being located within the probe holder assembly 12 to provide positional compensation for the probe tip 20 is that the probe tip 20 is prevented from being tilted relative to the surface being scanned, even when scanning an edge or scanning to an edge or corner of a slot. The slide 40 can be secured, such as midway between its travel extremes, with a thumb screw 27 shown in FIGS. 4 and 5 as located on the probe housing 28. The ability to immobilize the slide 40 with the thumb screw 27 is useful when testing and programming the probe assembly 10.

While the invention has been described in terms of a preferred embodiment, it is apparent that other forms could be adopted by one skilled in the art. For example, the physical configurations of the probe assembly 12, probe holder assembly 12 and probe tip 20 could differ from that shown, and various materials and processes could be used to fabricate and assembly their components. Therefore, the scope of the invention is to be limited only by the following claims.

The invention claimed is:

1. A method of inspecting a component having at least one slot on a perimeter thereof, the method comprising the steps of:

mounting a probe assembly to a robotic apparatus, the probe assembly comprising a holder assembly to which a probe tip is mounted, an eddy current coil within the probe tip and adjacent a first face thereof, a touch probe contact located at a second face of the probe tip, means for enabling relative movement between the probe tip and the holder assembly, and means for biasing the probe tip relative to the holder assembly in a direction parallel to the movement enabled by the enabling means;

placing the eddy current probe tip of the probe assembly into the slot; and causing the first face of the probe tip to contact and travel along the surface of the slot and causing the eddy current coil to electromagnetically inspect the slot for cracks in the surface thereof, the biasing means and the enabling means maintaining the first face of the probe tip in contact with the surface of the slot as the probe tip travels through the slot;

wherein the touch probe contact is electrically insulated from the probe tip and is electrically coupled to a connector on the holder assembly, and during the causing step contact between the touch probe contact and the surface of the slot results in electrical grounding and uploading the position of the probe tip to the robotic apparatus for enabling continuous adjustments of the position of the probe tip within the slot.

2. The method according to claim 1, wherein the enabling means comprises a slide and a slot that couple together first and second portions of the holder assembly.

3. The method according to claim 2, wherein the biasing means biases the first portion of the holder assembly relative to the second portion of the holder assembly.

4. The method according to claim 2, wherein the first portion of the holder assembly comprises electrical connectors electrically coupled to the touch probe contact and the eddy current coil of the probe tip.

5. The method according to claim 1, wherein the touch probe contact is a spherical ball.

6. The method according to claim 1, wherein the biasing means biases the first face of the probe tip in a direction normal thereto.

7. The method according to claim 1, wherein the probe assembly further comprises a probe unit comprising the probe tip and a probe unit connector to which the probe tip is mounted and by which the probe unit is removably coupled to the holder assembly.

8. The method according to claim 1, wherein the component is a rotating component of a turbomachine and the slot is one of a plurality of slots at a perimeter of the component and configured for mating with and securing airfoil members to the perimeter of the component.

9. The method according to claim 8, wherein the component is a turbine disk and the turbomachine is a gas turbine engine.

10. An inspection system for inspecting a component having at least one slot on a perimeter thereof, the inspection system comprising:

a probe assembly configured for mounting to a robotic apparatus, the probe assembly comprising a holder assembly to which a probe tip is mounted, an eddy current coil within the probe tip and adjacent a first face thereof, a touch probe contact located at a second face of the probe tip, means for enabling relative movement between the probe tip and the holder assembly, and means for biasing the probe tip relative to the holder assembly in a direction parallel to the movement enabled by the enabling means;

wherein the biasing means and the enabling means are adapted to maintain the first face of the probe tip in contact with a surface of the slot as the probe tip travels through the slot, the touch probe contact is electrically insulated from the probe tip and is electrically coupled to a connector on the holder assembly, and contact between the touch probe contact and the surface of the slot results in electrical grounding and uploading the position of the probe tip to the robotic apparatus for enabling continuous adjustments of the position of the probe tip within the slot.

11. The inspection system according to claim 10, wherein the enabling means comprises a slide and a slot that couple together first and second portions of the holder assembly.

12. The inspection system according to claim 11, wherein the biasing means biases the first portion of the holder assembly relative to the second portion of the holder assembly.

13. The inspection system according to claim 12, wherein the first portion of the holder assembly comprises electrical connectors electrically coupled to the touch probe contact and the eddy current coil of the probe tip.

14. The inspection system according to claim 10, wherein the touch probe contact is a spherical ball.

15. The inspection system according to claim 10, wherein the biasing means biases the first face of the probe tip in a direction normal thereto.

16. The inspection system according to claim 10, wherein the probe assembly further comprises a probe unit comprising the probe tip and a probe unit connector to which the probe tip is mounted and by which the probe unit is removably coupled to the holder assembly.

17. The inspection system according to claim 16, wherein the probe unit further comprises a stem that mounts the probe tip to the probe unit connector and defines a longitudinal axis of the probe unit.

18. The inspection system according to claim 17, wherein the first face of the probe tip at which the eddy current coil is located is a longitudinal face of the probe tip.

* * * * *